United States Patent

Hagen

[11] Patent Number: 5,933,243
[45] Date of Patent: Aug. 3, 1999

[54] DEVICE FOR COLOR MEASURING

[75] Inventor: Werner Hagen, Neuwied, Germany

[73] Assignee: Honeywell Inc., Minneapolis, Minn.

[21] Appl. No.: 08/875,392

[22] PCT Filed: Jan. 17, 1996

[86] PCT No.: PCT/EP96/00173

§ 371 Date: Oct. 15, 1997

§ 102(e) Date: Oct. 15, 1997

[87] PCT Pub. No.: WO96/24046

PCT Pub. Date: Aug. 8, 1996

[30] Foreign Application Priority Data

Feb. 4, 1995 [DE] Germany .......................... 195 03 763

[51] Int. Cl.⁶ .................................................. G01J 3/46
[52] U.S. Cl. ............................................................ 356/402
[58] Field of Search .......................... 356/402–411, 425, 356/445–448, 435, 73; 250/226, 548; 382/112, 141, 162; 702/85–107, 69, 191, 195, 171

[56] References Cited

U.S. PATENT DOCUMENTS 4,288,160  9/1981  Lodzinski .

FOREIGN PATENT DOCUMENTS 2805967  8/1979  Germany .

*Primary Examiner*—K P Hantis
*Attorney, Agent, or Firm*—Anthony Miologos

[57] ABSTRACT

A color measuring device measures the light transmitted through the material to be measured as well as the light reflected therefrom and the irradiated light and measures the color reflectivity in the various spectral ranges by dividing the reflected intensity by the difference between the irradiated and transmitted intensity. The calculation of the color reflectivity in the individual spectral ranges is thus corrected to the proper extent without the need to place color tiles behind a transparent material to be measured.

6 Claims, 4 Drawing Sheets

DEVICE FOR COLOR MEASURING

BACKGROUND OF THE INVENTION

1. Field of the Invention

The present invention relates generally to the field of papermaking and more specifically to a device for color measuring.

2. Description of the Related Art

EP 0 240 610 B1 shows a device for measuring humidity and density of a web-shaped material at which coherent electromagnetic radiation with different frequencies is directed to the material and the reflected and transmitted radiation is evaluated. Herewith the emitted and irradiated radiation is not sensed.

If the material under test as e.g. paper is not completely opaque, then color measuring raises some difficulties. Under laboratory conditions it is possible to fold the material under test repeatedly in order to achieve a complete opacity, whereas this is not possible with respect to moved single-layer webs on paper machines. To this respect it is therefor prior art to produce an artificial background. To this end colored tiles, the color of which is matched to the material under test to be measured, are brought behind the material under test. The disadvantage of this solution consists in that already with small distances between the material under test and the color tile an error arises in the color measuring. Moreover, the variety of papers which are produced on a machine is often very large, and, therefore, it is not always possible to back it by a color tile with the right color.

Departing from this prior art, it is therefor the object of the present invention to devise a color measuring device which, independent of the opacity and without the requirement of backing the material under test, allows an accurate color measurement.

BRIEF SUMMARY OF THE INVENTION

The solution of this object is achieved by an improvement to a device for the color measuring of materials under test, in particular paper webs. The device includes a light source arranged to generate light in a plurality of spectral ranges and means for splitting the light irradiated by the light source into a first and a second beam of light, the first beam directed onto the material under test. The device further includes a first measuring apparatus for receiving and generating signals representative of the intensity of the light reflected off of the material under test for each spectral range received, and a second measuring apparatus for receiving and generating signals representative of the intensity of the light of the second beam for each spectral range received and a color computer for receiving and processing the signals from the first and second measuring apparatus. The improvement comprises a third measuring apparatus arranged to receive light from the first beam that is transmitted through the material under test and to generate signals representative of the light received therethrough for each spectral range received, whereby the color computer receives and processes the signals from the third measuring apparatus by subtracting the signals received from the third measuring apparatus from the signals received from the second measuring apparatus, thereby forming a difference signal for each spectral range. The color reflectivity is determined by the color computer by dividing the difference signal for each spectral range from the signals received from the first measuring apparatus for the associated spectral range.

BRIEF DESCRIPTION OF THE SEVERAL VIEWS OF THE DRAWINGS

With respect to the figures of the attached drawing in the following the underlying problem of the invention and its solution shall be further described with respect to an embodiment whereby.

DETAILED DESCRIPTION OF THE INVENTION

Figure 1:
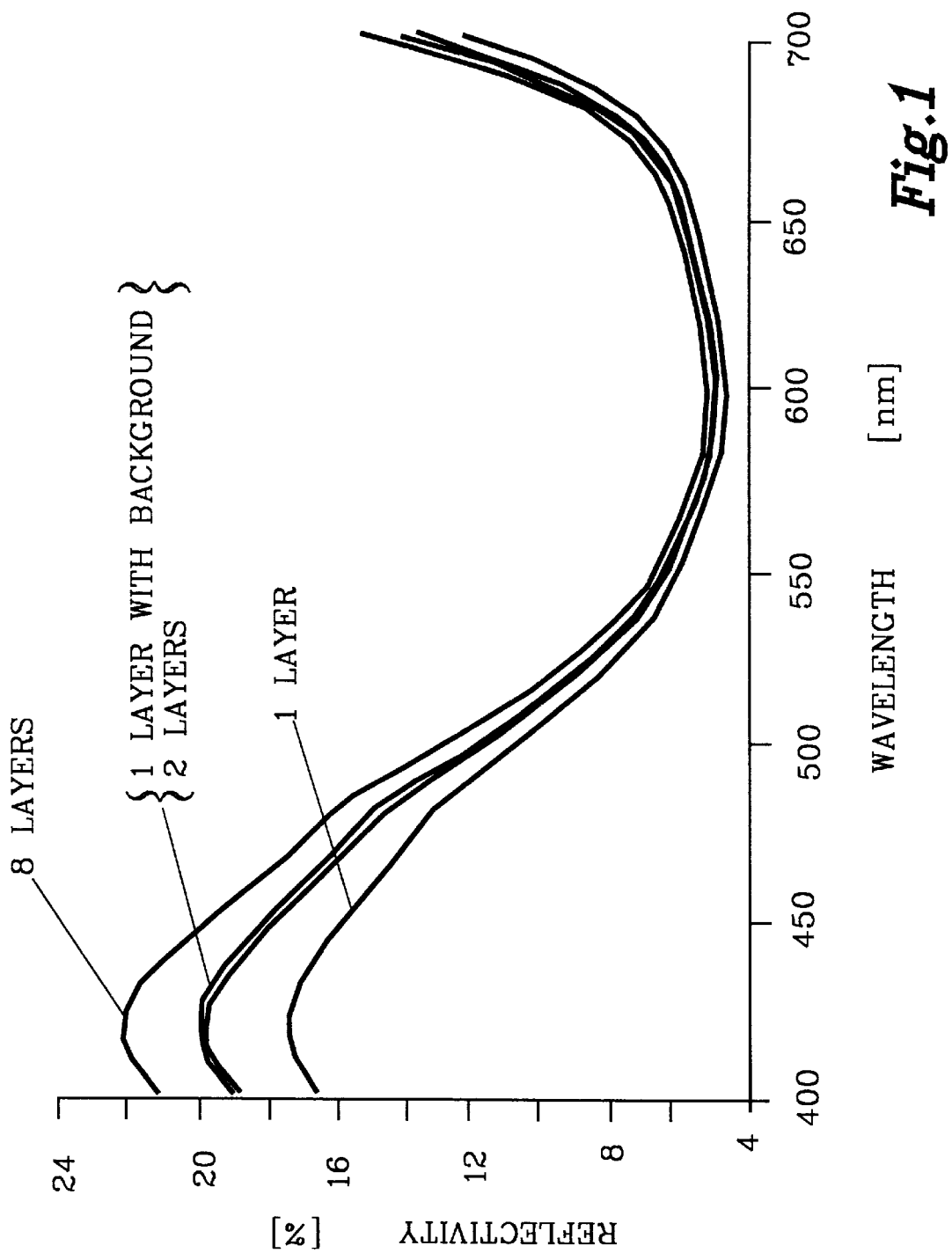
FIG. 1 shows the spectral reflectivity of a material under test as a function of the wavelength of the light with the thickness of the layer as a parameter.

From FIG. 1 it is discernible that over the spectral wavelength range being of interest at the color measuring, the reflectivity which is evaluated at color measuring shows strongly different values as a function of the thickness of the layer of the material under test to be measured.

Figure 2:
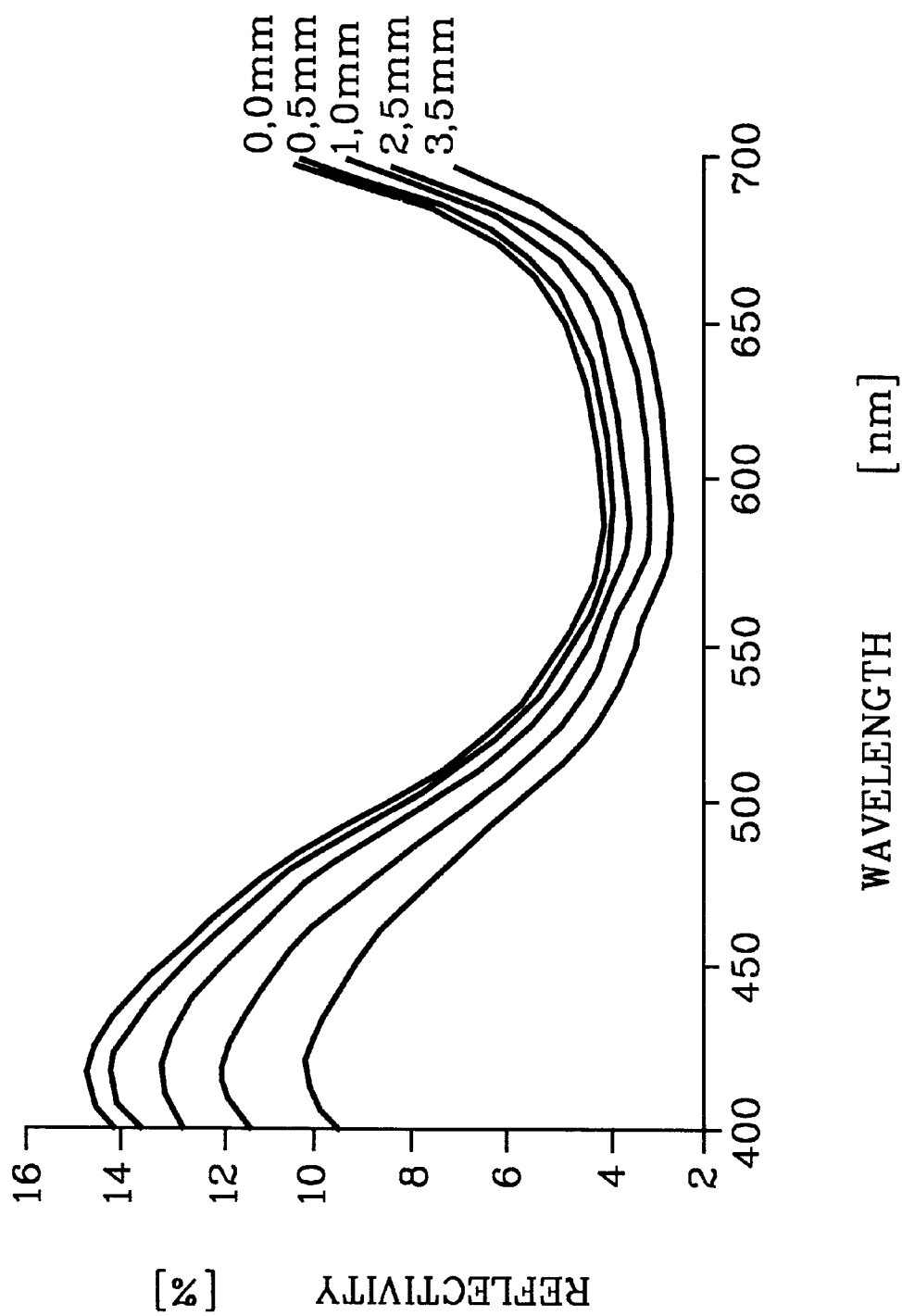
FIG. 2 shows the spectral reflectivity of a material under test as a function of the wavelength with the distance of its backing as a parameter.

FIG. 2 shows in the same way that at backing of the material under test with a selected color tile the reflectivity shows strongly different values as a function how large the distance is between the material under test and the color tile.

Figure 3:
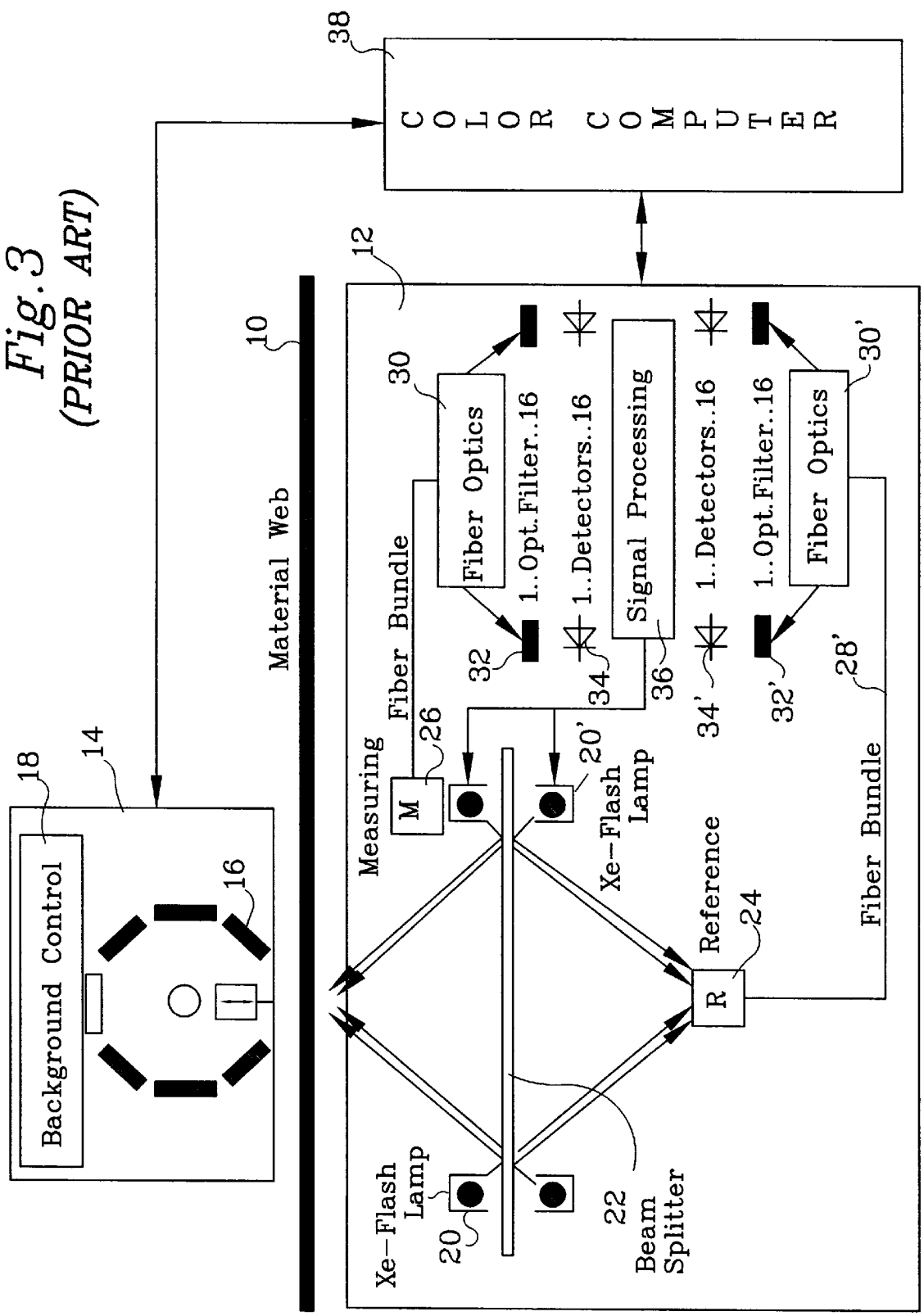
FIG. 3 shows a device for color measuring according to the prior art.

FIG. 3 shows a known device for color measuring which is subject of the above-mentioned disadvantages.

A material under test 10 preferably of paper extends between the lower portion 12 and the upper portion 14 of a measuring head which is travelling across the material under test 10 or is arranged stationarily with respect to it, respectively. Within the upper portion 14 color tiles 16 having different colors are arranged on an octagon which by means of a background controller 18 may be brought into a position where they are backing the material under test 10.

Within the lower portion 12 xenon flashlight ring lamp 20 is arranged, the light of which on one hand via a beam splitter 22 is reflected to the material under test 10 and on the other hand through the beam splitter 22 is impinging on a reference measuring location 24. The light reflected from the material under test 10 is sensed at a measuring location 26. Since the xenon flashlight ring lamp 20 has a spectrum ranging up to the UV range and the UV portion within the light projected onto the material under test 10 is producing light within the visible range in the event where the material under test contains a brightener substance which is sensed at the measuring location 26 and is tampering the measuring, a further xenon flashlight ring lamp 20' is arranged below and symmetrical to the beam splitter 22, and the beam splitter 22 is provided with the behaviour of a UV filter. Both of the ring lamps 20, 20' are alternately operated so that light is alternately received at the real measuring location 26 as well as at the reference measuring location 24 with the light not containing the UV portion or the light produced by the UV portion, respectively, whereby accuracy of the measuring is improved.

The light radiation received at the measuring location 26 and at the reference measuring location 24 each via fiber bundles 28, 28' and a fiber optics 30, 30' is fed to optical filters 23, 23', behind which photodiodes 34, 34' are arranged, which sense the signals within the different spectral ranges. Those signals are fed to a computer 38 via a signal processing means 36 with said computer calculating the color reflectivity within the different spectral ranges from the relation between the reflected intensity and the irradiated intensity. The computer controls the selection of the according color tile 16 via the background controller 18. Additionally, it controls the alternate switching-on of the ring lamps 20, 20'.

Figure 4:
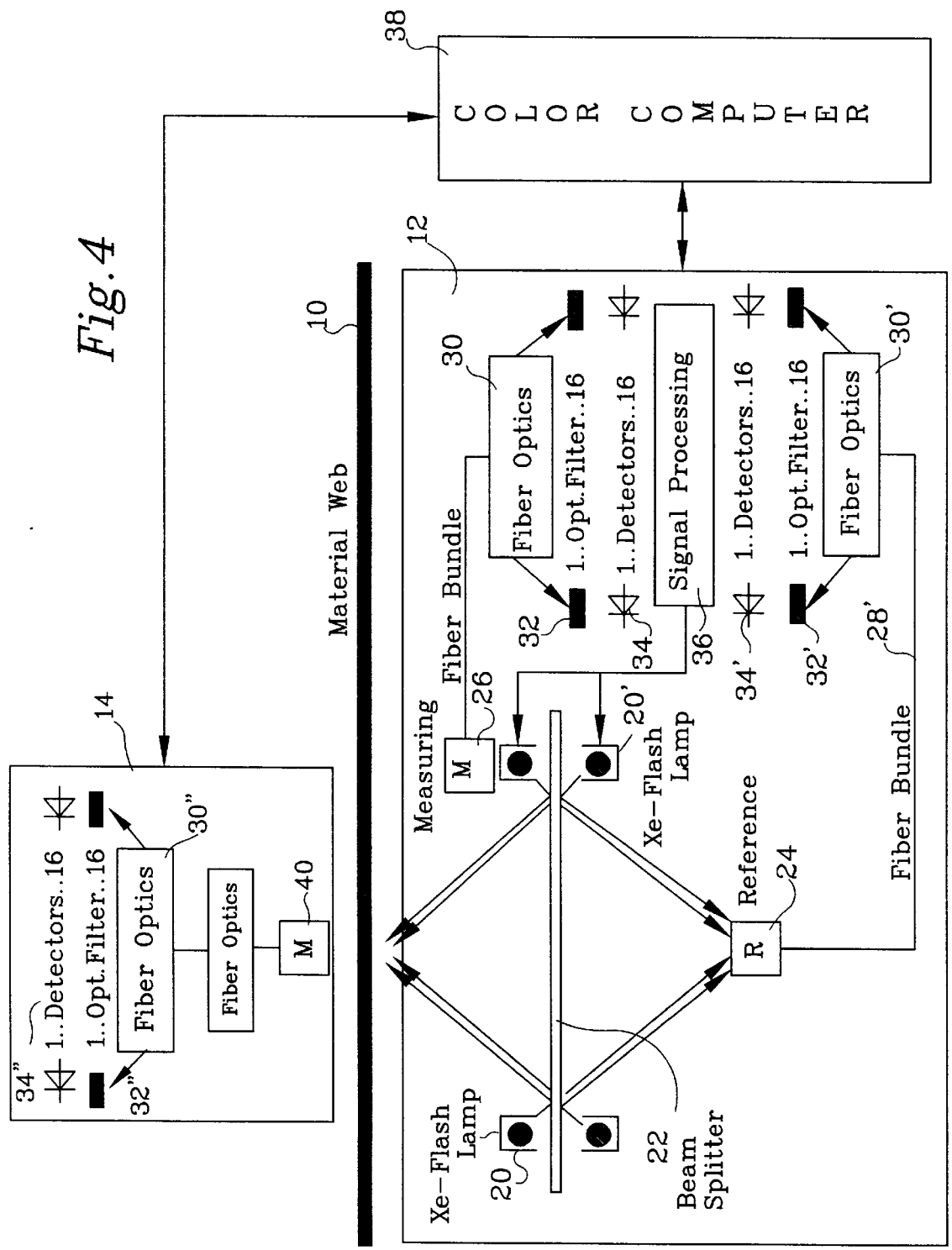
FIG. 4 shows the improved device for color measuring of the present invention.

The inventive device according to FIG. 4 is distinguished over the known device according to FIG. 3 by the provision of an additional measuring location 40 within the upper portion 14 of the measuring carriage for the reception of light being transmitted through the material under test, whereat the measured signals again via a fiber bundle 28" and a fiber optics 30" are fed to optical filters 32", behind which photo diodes 34" are arranged. The signals of the photodiodes 34" if necessary after an according signal conditioning are fed to the computer 38 which calculates the color reflectivity within the different spectral ranges according to the following relationship:

$$\text{Color Reflectivity} = \frac{\text{reflected intensity}}{\text{irradiated intensity} - \text{transmitted intensity}}$$

By this calculation the color reflectivity is corrected in the right way. Herewith it is to note that the correction for each wavelength is individually done.

The present invention has been described with particular reference to the preferred embodiments thereof. It will be obvious that various changes and modifications can be made therein without departing from the spirit and scope of the invention as defined in the appended claims.

What is claimed is:

1. An improved device for the color measuring of materials under test, in particular of paper webs, the device measuring color reflectivity and including a light source arranged to generate light in a plurality of spectral ranges, means for splitting the light irradiated by the light source into a first and a second beam of light, said first beam of light directed onto the materials under test and a first measuring apparatus for receiving and generating signals representative of the intensity of the light reflected by the materials under test for each spectral range received and a second measuring apparatus for receiving and generating signals representative of the intensity of the light of said second beam of light for each spectral range received and an evaluation device for receiving and processing the signals from said first and said second measuring apparatus to determine the color reflectivity of the materials under test, the improvement comprising:

a third measuring apparatus arranged to receive the light from said first beam of light that passes through the materials under test and to generate signals representative of the intensity of light received for each spectral range, whereby the evaluation device receives the signals from said third measuring apparatus and in the determination of the color reflectivity for each spectral range of said plurality of spectral ranges the signal from said third measuring apparatus is subtracted from the signal from said second measuring apparatus.

2. An improved device for color measuring as claimed in claim 1, wherein said evaluation device is a computer and said computer determines said color reflectivity by dividing said signals from said first measuring apparatus by said signals from said second measuring apparatus whereby in said improved device said computer further receives said signals from said third measuring apparatus and said signals from said third measuring apparatus are first subtracted from said signals from said second measuring apparatus developing a difference signal and the color reflectivity is thereby determined by dividing said signals from said first measuring apparatus by said difference signal.

3. An improved device for color measuring as claimed in claim 2, wherein the device further includes a measuring head and said measuring head includes a first portion and a second portion with said materials under test located therebetween, said first portion containing said light source and said first and said second measuring apparatus therein whereby in said improvement, said third measuring apparatus is contained in said second portion.

4. An improved device for color measuring as claimed in claim 3, wherein said first measuring apparatus includes measuring location optically connected to a fiber optic network by a fiber optic bundle and said fiber optic network is optically connected to a plurality of photodiodes, said photodiodes electrically connected to said computer and optically connected to said optical filters, and responsive to said measuring location receiving said light reflected from said materials under test, said light received is transmitted via said fiber optic bundle to said fiber optic network and said optical filters to said photodiodes whereby said photodiodes generate and transmit to said computer electrical signals representative of the intensity of light received for each spectral range of said plurality of spectral ranges.

5. An improved device for color measuring as claimed in claim 3, wherein said second measuring apparatus includes a measuring location optically connected to a fiber optic network by a fiber optic bundle and said fiber optic network is optically connected to a plurality of photodiodes, said photodiodes electrically connected to said computer and optically connected to said optical filters, and responsive to said measuring location receiving said second beam of light, said light received is transmitted via said fiber optic bundle to said fiber optic network and said optical filters to said photodiodes, whereby said photodiodes generate and transmit to said computer electrical signals representative of the intensity of light received for each spectral range of said plurality of spectral ranges of said second beam of light irradiated by said light source.

6. An improved device for color measuring as claimed in claim 3, wherein said third measuring apparatus includes a measuring location optically connected to a fiber optic network by a fiber optic bundle and said fiber optic network is optically connected to a plurality of photodiodes, said photodiodes electrically connected to said computer and optically connected to said optical filters, and responsive to said measuring location receiving said light passed through said materials under test, said light received is transmitted via said fiber optic bundle to said fiber optic network and said optical filters to said photodiodes, whereby said photodiodes generate and transmit to said computer electrical signals representative of the intensity of light received for each spectral range of said plurality of spectral ranges.

* * * * *